United States Patent [19]

Kalman

[11] Patent Number: 4,927,966
[45] Date of Patent: May 22, 1990

[54] 2-MERCAPTOMETHYLGLUTARIC ACID DERIVATIVES

[75] Inventor: Thomas I. Kalman, East Amherst, N.Y.

[73] Assignee: The Research Foundation of State University of New York, Albany, N.Y.

[21] Appl. No.: 58,035

[22] Filed: Jun. 4, 1987

[51] Int. Cl.$^5$ .................... C07C 55/12; C07C 149/20; C07F 1/12; C07F 15/04
[52] U.S. Cl. ...................................... 562/594; 556/49; 556/61; 556/114; 556/115; 556/116; 556/131; 556/132; 556/134; 556/136; 556/137; 556/147; 556/148; 558/251; 558/255; 558/256; 558/257; 560/9; 560/17; 560/147; 560/154; 562/431; 562/578
[58] Field of Search ...................... 562/594, 431, 578; 514/574, 492, 494–495, 499, 501, 502, 505, 513, 532–535, 544, 546–548, 550, 557, 567; 556/49, 61, 114–116, 131–132, 134, 136–137, 147–148; 560/195, 193, 9, 17, 147, 154; 558/251, 255, 256–257

[56] References Cited

U.S. PATENT DOCUMENTS 3,205,268  9/1965  Rosenwald .................... 562/594 X
3,271,248  9/1966  Renault et al. ................. 562/594 X
4,172,207  10/1979 Mack ................................ 560/147

OTHER PUBLICATIONS

Chemistry and Biology of Pteridines, 1986, pp. 583–586, T. I. Kalman et al.
Biochemical and Biophysical Research Communications, pp. 292–297, vol. 144, V. Whitehead et al, Apr. 1987.
Proc. Amer. Assoc. Cancer Res., 28, 272 (Apr. 1987), V. M. Whitehead et al.

Primary Examiner—Werren B. Lone
Assistant Examiner—Vera C. Clarke
Attorney, Agent, or Firm—Michael L. Dunn; William J. Crossetta

[57] ABSTRACT

New compounds having utility for enhancing the activity of antifolates are disclosed of the formula:

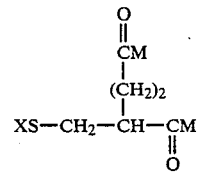

wherein X is selected from hydrogen

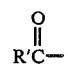

and R''—; R' is selected from alkyl, alkenyl, alkynyl, substituted and unsubstituted aryl, and substituted and unsubstituted heterocyclic aryl; R'' is selected from

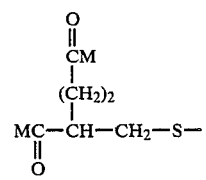

and R'S; M is selected from OR and secondary amine; and R is selected from hydrogen, alkyl, acyloxymethyl, substituted and unsubstituted aryl, substituted and unsubstituted heterocyclic aryl, amino cation and metal cation.

16 Claims, No Drawings

2-MERCAPTOMETHYLGLUTARIC ACID DERIVATIVES

This invention was made in part with government support under Grant Number CA R01 35212 awarded by the National Institutes of Health, Department of Health and Human Services. The government has certain rights in this invention.

BACKGROUND OF THE INVENTION

There has been a continuing need for effective chemotherapeutic agents and drugs embodying chemotherapeutic agents which are effective in inhibiting the growth of cancer. One type of chemotherapeutic agent which has demonstrated cancer inhibiting qualities is the folic acid antagonist (antifolate). Antifolates are thought to be effective chemotherapeutic agents because various coenzyme forms of folic acid are essential for biosynthesis of the thymine and purine precursors of DNA. Thus, suppressing such coenzyme forms of folic acid is considered as suppressing materials essential for cell division and cellular proliferation. Typically, antifolate drugs currently being used as chemotherapeutic agents act to interfere with microbial folic acid biosynthesis or act by inhibition of bacterial, plasmodial or mammalian dihydrofolate reductases in the animal body. A problem persists, however, with use of current antifolates in that they typically display poor penetration into solid tumors, particularly of the brain thus manifesting low efficiency. Current antifolates also display severe toxicity to rapidly proliferating normal tissues thus presenting a major limitation to their use in the treatment of malignancies in warm blooded animals.

Folates occur in nature predominantly as poly-gamma-glutamates containing 3-7 or even more glutamate residues. The occurrence of folate polyglutamates is universal. These metabolic forms have been identified in many species of animals as well as in all human tisues, blood cells and lymphocytes. The metabolically functional forms of folates are polyglutamylated tetrahydrofolates, serving as cofactors for a variety of enzyme catalyzed reactions inside the cell. The enzyme responsible for the formation of poly-gamma-glutamates is folylpolyglutamate synthetase. Its vital function is evidenced by the inability of mutant mammalian cells lacking this enzyme to survive in the absence of thymidine, glycine and adenine, which are the products of folate requiring metabolic pathways.

Though the essential role of folate polyglutamylation is not fully understood, it has been found that many folate requiring enzymes have higher affinity to their polyglutamylated cofactors than to the corresponding monoglutamates. Long chain polyglutamyl derivatives of methotrexate (MTX), an effective antiproliferative agent, enhance the intracellular retention of the drug and since "free" exchangeable MTX, in excess of that bound to dihydrofolate reductase, is required for complete inhibition of the enzyme, polyglutamylation helps to maintain the needed intracellular drug level. In addition to dihydrofolate reductase, the primary target of MTX, polyglutamate derivatives of the drug are also inhibitory to other essential folate requiring enzymes. Thus, compounds which are able to protect the polyglutamates of MTX from metabolic degradation to shorter chain derivatives, would have the indirect effect of inhibiting cancer by enhancing (potentiating) the activity of MTX.

In high dose MTX cancer treatment programs, wherein the patient is exposed to severe systemic toxicity risk with dosages of MTX approaching or exceeding the lethal level, Leucovorin is typically used as a "rescue" agent to rescue normal cells and thereby prevent toxicity. Thus, compounds which have a dual effect in that they enhance the activity of MTX in the cancer tumor while at the same time enhancing the effect of Leucovorin in protecting normal cells would be of significant pharmacological value.

Methotrexate and other antifolates have also been identified as active agents in the treatment of psoriasis but MTX is of such severe systemic toxicity that treatment to attain enough MTX at the sites of the psoriasis usually involves a toxic risk to the patient. Again, compounds which enhance the activity of MTX would have an indirect effect, being to inhibit psoriasis.

Methotrexate and other antifolates are additionally known as effective immunosuppressive agents thus having utility in preventing graft-versus-host reaction that result from tissue transplants, and utility in the management of dermatomyositis, arthritis, and other inflammatory diseases. As use of methotrexate and other antifolates as immunosupressive agents involves a systemic toxicity risk to the patient, compounds which enhance the activity of MTX and/or other antifolates would have a beneficial effect in such applications.

There has also been a continuing demand for new complexing agents which are capable of complexing with metal cations in such manner as to foster removal of such cations from various solutions. New agents are always in commercial demand because of the many different process parameters and formulations in which they may be used and the variation in characteristics that may be imposed upon such processes or formulations by the complexing agent.

The ability to complex pharmacologically active metals such as gold, copper and the like provides a further activity dimension to such compounds. Gold, particularly in the form of gold sodium thiomalate, is a drug of choice in the treatment of rhumatoid arthritis. Gold complex compounds which can provide the active gold metal together in a complex structure, which structure might be used for combination therapy, are thus pharmacologically desirable.

An object of this invention is to provide new compounds which selectively inhibit gamma-glutamyl hydrolases.

Another object of this invention is to provide new compounds useful as intermediates for the production of compounds which inhibit gamma-glutamate hydrolases.

A still further object is to provide new compounds which are precursors (prodrugs) for the in vivo conversion to compounds which inhibit gamma-glutamyl hydrolases.

A further object is to provide new compounds which enhance the activity of methotrexate and other antifolates.

An additional object of this invention is to provide new compounds useful as antidotes of carboxypeptidase G.

These and other objects of the invention will become apparent from the following description of the invention.

DESCRIPTION OF THE INVENTION

This invention relates to new 2-mercaptomethylglutaric acid derivatives; to compositions comprising these derivatives; to methods of use of these derivatives to enhance the biological activity of folate antagonists such as methotrexate and other drugs; and, to their use as effective complexing agents.

In accordance with this invention, new 2-mercaptomethylglutaric acid derivatives are provided of the formula:

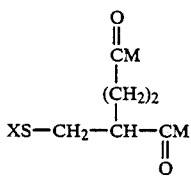

wherein X is selected from hydrogen,

and R''—; R' is selected from hydrogen, alkyl, alkenyl, alkynyl, substituted and unsubstituted aryl, and substituted and unsubstituted heterocyclic aryl; R'' is selected from

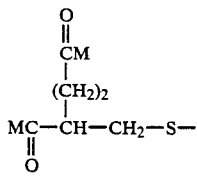

and R'S; M is selected from OR, and secondary amine; and R is selected from hydrogen, alkyl, acyloxymethyl, substituted and unsubstituted aryl, substituted and unsubstituted heterocyclic aryl, amino cation and metal cation.

Further, in accord with the invention, new compositions, particularly pharmaceutical compositions, are provided which contain the compounds of the invention.

In addition, a method of the invention is provided wherein one or more of the afore-described compounds is administered to a cancer-containing warm-blooded animal.

In another method of the invention one or more of the afore-described compounds is administered to a psoriasis containing warm-blooded animal.

In another further method of the invention, one or more of the described compounds is administered to an arthritis containing warm-blooded animal.

In still another method of the invention, one or more of the afore-described compounds is administered to a solution to complex therefrom metal ions.

Within the description of the compounds of the invention, particularly the designation R, R', R'', M and X, by the term alkyl, alkenyl and alkynyl is meant alkane, alkene and alkyne hydrocarbon substituents having from 1 to about 20 carbon atoms. Substituents can be straight chained, or branched and include isomers thereof. Thus the term alkyl includes methyl, ethyl, n-propyl, i-propyl, n-butyl, i-butyl, t-butyl, pentyl, hexyl, heptyl and the like up to about 20 carbon atoms. Similarly, the term alkenyl includes unsaturated hydrocarbons having one or more double bonds therein such as ethene, propene, butene, pentene and the like up to about 20 carbon atoms. Also similarly the term alkynyl includes hydrocarbons having one or more triple bonds therein such as acetylene, methyl acetylene, ethyl acetylene and the like up to about 20 carbon atoms.

By the term acyloxymethyl is meant alkyl carbonyl oxy methyl groups up to about 20 carbon atoms in length including acetoxymethyl, pivaloyloxymethyl and the like.

By the term aryl is meant those cyclic aromatic structures which include benzene, napthalene and the like, up to a total of about 10 carbon atoms. Attachment of the aryl group to the basic structure can be by direct attachment to the ring or through a substituent attached to the ring.

By the term heterocyclic aryl is meant those hetero aromatic structures which contain at least one of nitrogen, oxygen or sulfur in the ring structure, which include pyridine, pyrimidine, quinoline, thiophene, indole, furan and the like up to about 10 carbon atoms. Attachment of the heterocyclic group can be by direct attachment from the ring to the basic structure or through a substituent attached to the ring.

The substituents which can be attached to the aryl or heterocyclic aryl moiety can be selected from alkyl, alkenyl, alkynyl and aryl and can comprise the means of attachment to the base structure, provided the total number of carbon atoms appended to the base structure for the moiety does not exceed about 20.

By the term secondary amine is meant compounds of the formula:

wherein R''' is selected from hydrogen, alkyl and aryl up to about 20 carbon atoms. By amino cation is meant the positively charged protonated form of the above-identified amino.

By the term metal cation is meant the positively charged ion of alkaline metal, alkaline earth, transition metals, gold, platinum and mixtures thereof. By alkali metal is meant metals of Group IA of the periodic table of elements comprising lithium, sodium and potassium. By alkaline earth metal is meant metals of Group IIA of the periodic table comprising magnesium, calcium and strontium. By transition metal is meant chromium, manganese, iron, cobalt, nickel, copper and zinc.

Typical compounds falling within the structure of the claimed invention include: 2-mercaptomethylglutaric acid, bis(2,4-dicarboxy-1-butyl) disulfide, S-benzoyl-2-mercaptomethylglutaric acid, S-acetyl-2-mercaptomethylglutaric acid, S-propionyl-2-mercaptomethylglutaric acid, S-butyryl-2-mercaptomethylglutaric acid, S-isobutyryl-2-mercaptomethylglutaric acid, S-pivaloyl-2-mercaptomethylglutaric acid, dimethyl 2-mercaptomethylglutarate, diethyl 2-mercaptomethylglutarate, diisopropyl 2-mercaptomethylglutarate, ditertiarybutyl 2-mercaptomethylglutarate, diacetoxymethyl 2-mercaptomethylglutarate, dipivaloyloxymethyl 2-mercaptomethylglutarate, 2-mercaptomethylglutaramide, 2- mercaptomethyl-N,N'-dimethylglutaramide and the like.

Typically, the preparation of the reducing agent compounds of the invention can be attained through several routes. The product obtained is usually a mixture of the D,L isomers and can be used without separation. Generally higher yields and convenient product isolation is attained with a synthesis route in accordance with the following schematic:

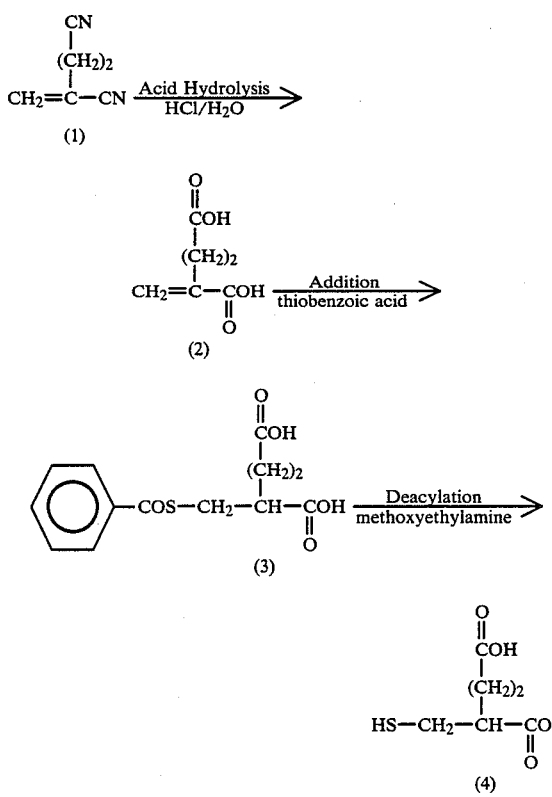

In the above schematic, it should be readily apparent that 2-methyleneglutaric acid (compound 2) is known in the prior art. I have included the manufacture of compound 2 only because of its limited commercial availability and the relative convenience of manufacturing the compound from readily available 2,4-dicyano-2-butene (compound 1) by simple and rapid acid hydrolysis with modest temperature.

The addition of thiobenzoic acid to 2-methyleneglutaric acid in order to form S-benzoyl-2-mercaptomethylglutaric acid (compound 3) is also a convenient approach to the final compound which provides the desired product in reasonable yields. It was found that the reaction proceeds efficiently at lower temperatures (0°–10° C.), in an appropriate solvent such as acetone.

The deacylation of the benzoic acid moiety from the main structure of the compound to form the active 2-mercaptomethylglutaric acid compound (compound 4), directly responsible for selectively inhibiting gamma-glutamyl hydrolases, is also easily achievable. Generally, it was found that reacting the S-benzoyl-2-mercaptomethylglutaric acid, at lower temperature (0°–10° C.) with a suitable amine such as 2-methoxyethylamine and extracting the 2-mercaptomethylglutaric acid results in yields of product exceeding 90%.

Upon isolating the 2-mercaptomethylglutaric acid, attainment of the various selected X and M moieties can generally be achieved by multiple means.

To attain an  moiety on the sulfur of compound (4) entails reacting compound (4) with an appropriate R' substituted anhydride or acylhalide in accord with the following:

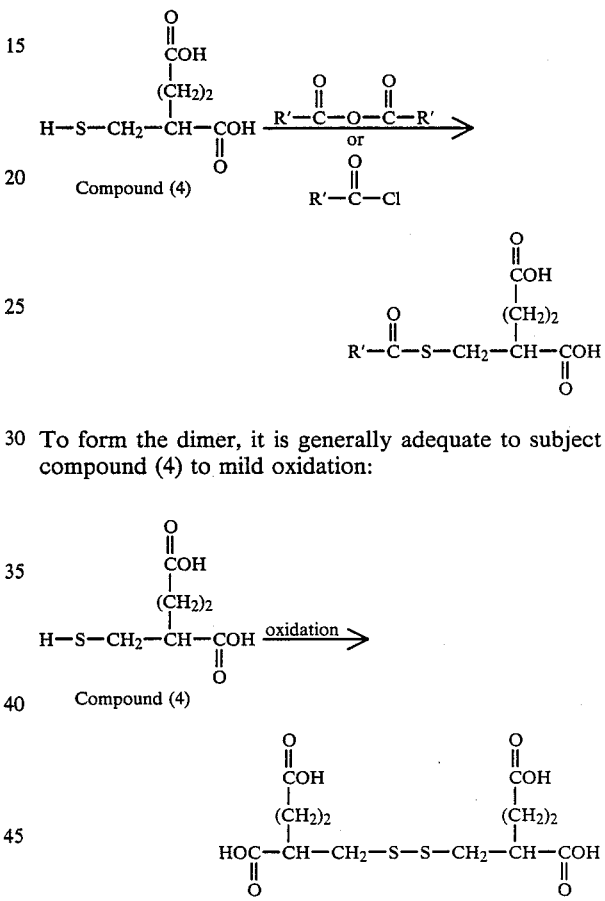

To form the dimer, it is generally adequate to subject compound (4) to mild oxidation:

Substitution of an R'S moiety on the sulfur of compound (4), can be easily accomplished by thiol-disulfide exchange using an excess of R'—S—S—R'.

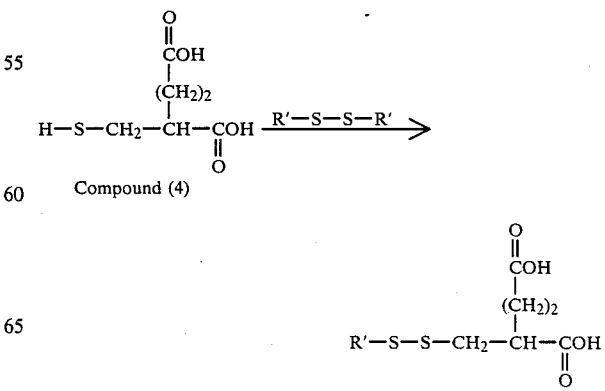

Substitution of the hydroxy group on the carboxyl moieties of the 2-mercaptomethylglutaric acid is again simple and efficiently achieved by multiple means.

To substitute an OR moiety on a carboxyl group, where R is selected from alkyl, aryl and heterocyclic aryl can be achieved by esterification with the corresponding alcohol in the presence of an acid catalyst:

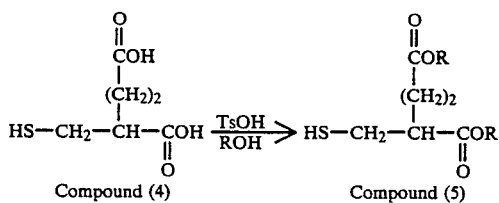

Compound (4) → Compound (5)

To substitute a secondary amine can be achieved by reaction of the substituted compound (5) with an appropriate secondary amine:

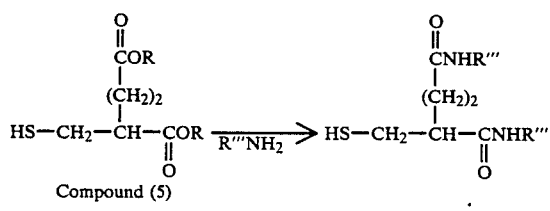

Compound (5)

To substitute an amino cation or metal cation can be achieved by simple reaction of compound (4) with the equivalent amount of the cation. Heavier metal cations will readily substitute for the lighter metals. Indeed, the ability of the acid to complex metal cation is so effective that an alternate utility of the acid, as a complexing agent, is a stated commercial utility of my invention.

To substitute an acyloxymethyl moiety can be achieved by alkylation with the corresponding methyl chloride:

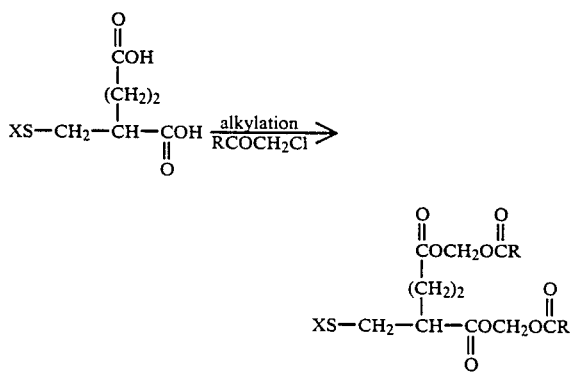

As above-described, the compounds of the invention have a particular effectiveness in complexing amino and metal cation. Thus, one method of the invention is the complexing of a metal cation using the compounds of the invention. In such utility, a compound of the invention would be contacted directly with a solution containing the cation to be complexed. Generally, it is preferred to use the compound wherein M is OH, but various of the metal cation compounds of the invention can be used to complex metals generally heavier than they.

Though the complexing of amino and metal cation is a formidable utility, these compounds also have a particular ability to enhance the activity of antifolates such as MTX. I believe that such an enhancing effect is achieved by inhibiting peptidases from preferentially catalyzing the hydrolysis of N-acylglutamate amide bonds including, in particular, gamma-glutamyl hydrolase enzymes of the carboxypeptidase type, with a preference for cleaving gamma-glutamyl-glutamate linkages typically present in folate and antifolate polyglutamates. This ability to enhance the activity of antifolates, particularly MTX, in many applications is synergistic in that it exceeds calculated additive effect.

Thus, another method of the invention comprises administering a compound of the invention to a cancer, psoriasis and/or arthritis containing warm blooded animal alone or in combination with an antifolate. For such utilities, though the end result is different, the methods generally usable are similar.

As previously discussed, one method of the invention comprises the inhibition of the growth of cancer and psoriasis. In accordance with such method, a warm blooded animal containing cancer or psoriasis is administered an effective growth inhibiting amount of a pharmaceutical composition comprising at least one compound of the invention. Arthritis treatment would comprise administering an effective immunosuppressing amount of at least one compound of the invention, alone or in combination with an antifolate such as MTX or aminopterin.

The quantity of the compound sufficient for treatment of cancer tumors, arthritis and psoriasis varies depending upon the size of the warm blooded animal involved, upon the type of ailment and upon the species of the animal involved. In general, for most applications, the effective growth inhibiting concentration of the compound of the invention usually ranges between about 0.5 and 1500 milligrams per kilogram of body weight of the organism being treated. The preferred concentration is between about 1 and about 300 milligrams per kilogram of body weight of the organism being treated. In general, large animals require less of any pharmaceutical compound per kilogram of body weight than smaller animals.

Any suitable dosage may be given in the method of the invention. The type of and the amount of dosage will vary widely depending on the species of the warm blooded animal, body weight, and type of ailment being treated. Generally, a dosage up to about 500 milligrams per kilogram of body weight is suitable. Generally, the dosage in man is lower than for small warm blooded mammals such as mice. A dosage unit may comprise a single compound of the invention or mixtures thereof with other compounds of the invention, antifolates or other growth inhibiting compounds. The dosage unit can also comprise diluents, extenders, carriers, and the like. The unit may be in solid or gel form such as pills, tablets, capsules, and the like or in liquid form suitable for oral, rectal, topical, or parenteral administration.

The method of treatment may be any suitable method which is effective in treatment of the particular ailment which is under treatment. Treatment may be oral, rectal, topical, parenteral, and the like. The method of applying an effective amount also varies depending on the ailment being treated. It is believed that parenteral treatment by intravenous, subcutaneous, or intramuscular application, formulated with an appropriate carrier, additional growth inhibiting compound(s), antifolate(s) or diluent to facilitate application, will be the preferred method of administering the compounds of the invention in warm blooded animals. Since toxicity is a major problem with treatment by MTX type drugs, it is contemplated that a combined treatment utilizing an antifolate such as MTX in combination with the compounds of the invention would be beneficial. Such combined treatment may comprise systemic administration of the MTX and local application of the compounds of the invention at the cancer, arthritis and/or psoriasis sites to potentiate the local effect and allow reduced systemic toxic risk.

EXAMPLE I

Preparation of S-Benzoyl-2-mercaptomethylglutaric Acid

To a cooled solution (5° C.) of thiobenzoic acid (5.5 g, 39.8 mmol) in acetone (75 mL), was added 2-methyleneglutaric acid (5.25 g, 36.4 mmol) with stirring. To the resulting solution, 4-dimethylaminopyridine (0.5 g, 4.1 mmol) was added and the solution was stirred for 5 hours at 5° C. The temperature was slowly raised to 60° C. and refluxed for 20 hours. The resulting solution was treated with activated charcoal (1 g) and filtered. The clear solution was evaporated to a thick liquid and cold distilled water (100 ml) was added with rapid stirring. The white precipitate formed was filtered and suspsended in a saturated aqueous solution of $NaHCO_3$. After stirring for 15 minutes, the suspension was filtered and the clear filtrate extracted with three portions of EtOAc. The aqueous fraction was then acidified with 18% HCl. The white precipitate formed was collected by filtration, washed with cold distilled water, and dried at 50° C. The crude product was crystallized from aqueous ethanol to yield white shiny crystals, representing a yield of 7.71 g (75%) of the captioned product (mp 144° C.).

EXAMPLE II

Preparation of 2-Mercaptomethylglutaric Acid

S-Benzoyl-2-mercaptomethylglutaric acid (2 g, 7.08 mmol) was added with stirring to 2-methoxyethylamine (20 mL) kept at 0°–5° C. The resulting solution was stirred for 2 hours at 0° C. and at 30° C. for 1 hour. The thick viscous liquid was evaporated at 60° C. under vacuum to a transparent gel. The residue was dissolved in oxygen-free water (40 mL) and extracted with three portions of EtOAc. The aqueous fraction was acidified with 18% HCl and reextracted with EtOAc. The EtOAc layer was dried over $Na_2SO_4$ and evaporated to a thick gel. The residue was dissolved in a mixture of EtOAc/hexane and cooled to −18° C. overnight. The white precipitate formed was collected by filtration, washed and dried under vacuum at room temperature to yield, 1.16 g (91.8%) of the captioned product (mp 75° C.)

EXAMPLE III

Transformed human lymphocytes (cancer cells) were incubated at a density of 5 million cells in 2 ml of culture medium. Human diploid fibroblasts (normal cells), in confluence, were incubated in 3 ml of culture medium. In each instance, the culture medium consisted of Eagle's minimal essential medium (MEM) containing 10% fetal calf serum with added glycine, adenosine and thymidine. Incubations were at 37° C. in 95% $O_2$+5% $CO_2$ for 24 hours in the presence of 1.0 μM of radioactive labelled ($^3H$)-methotrexate. The medium was removed from the incubated cells and fresh MEM was added. 2-Mercaptomethylglutaric acid (MMGA) was added to various of the test cultures in concentrations of 0.1 mM (cancer cells) and 0.4 mM (normal cells) and incubation was continued for an additional 24 and 48 hours. The cells were harvested, counted, lysed by sonication and protein was precipitated with 10% trichloracetic acid. The supernatant was frozen at −20° C. Methotrexate and methotrexate polyglutamates containing 2–6 glutamate residues were separated out by HPLC. The results are set out in Table I.

As can be seen, the addition of MMGA, in either instance of incubation time length, resulted in a significant percentage increase of long chain glutamate residues, thus confirming inhibition of intracellular gamma-glutamyl hydrolase.

EXAMPLE IV

Aqueous solutions of 0.005M and 0.01M $ZnCl_2$, in the presence and absence of 0.01M 2-mercaptomethylglutaric acid (MMGA) were titrated by addition of 0.01M potassium hydroxide in portions of 0.1 equivalents. Potentiometric titrations were performed using a pH meter equipped with a combination glass electrode. In the absence of MMGA, addition of 0.5 equivalents of 0.01M potassium hydroxide to the $ZnCl_2$ solutions caused the precipitation of the water insoluble $Zn(OH)_2$ within a pH change of one (1) unit. In the presence of MMGA, no precipitation of $Zn(OH)_2$ occurred even with the addition of several equivalents of potassium hydroxide through a rise in pH of six (6) units. The titration results were consistent with the presence of 2:1 and 1:1 complexes between MMGA and the zinc ion.

TABLE I

| | | Inhibition of Long Chain Degradation | | | | | | | |
|---|---|---|---|---|---|---|---|---|---|
| Test Cells | MMGA (mM) | Incubation (hrs) | No. of GLU Residues (%) | | | | | | Ratio $\frac{GLU_5 + GLU_6}{GLU_3 + GLU_4}$ |
| | | | 1 | 2 | 3 | 4 | 5 | 6 | |
| Cancer | — | 48 | 2.4 | 3.1 | 17.3 | 32.4 | 42.7 | 2.1 | 0.90 |
| Cancer | 0.1 | 48 | 2.2 | 2.3 | 8.5 | 17.6 | 67.0 | 2.3 | 2.66 |
| Cancer | — | 72 | 11.0 | 8.4 | 24.8 | 29.6 | 24.4 | 1.8 | 0.48 |
| Cancer | 0.1 | 72 | 7.0 | 3.3 | 8.9 | 15.9 | 62.1 | 2.1 | 2.61 |
| Normal | — | 48 | 2.8 | 1.9 | 8.5 | 25.8 | 55.6 | 5.4 | 1.78 |
| Normal | 0.4 | 48 | 1.8 | 1.4 | 3.2 | 8.5 | 81.0 | 4.2 | 7.27 |
| Normal | — | 72 | 4.7 | 4.0 | 13.5 | 26.6 | 48.5 | 2.6 | 1.28 |
| Normal | 0.4 | 72 | 3.0 | 1.5 | 3.3 | 5.1 | 78.4 | 5.7 | 10.36 |

What is claimed is:
1. A compound of the formula:

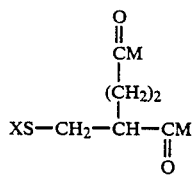

wherein X is selected from hydrogen, R'C— and R"—; R' is selected from alkyl, alkenyl, alkynyl, substituted and unsubstituted aryl; R" is selected from

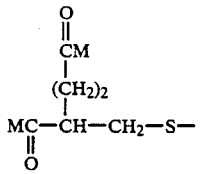

and R'S; M is selected from OR and secondary amine; and R is selected from hydrogen, alkyl, acyloxymethyl, substituted and unsubstituted aryl, amino cation and metal cation.

2. A compound of claim 1 wherein M is OR.
3. A compound of claim 2 wherein X is hydrogen.
4. A compound of claim 3 selected from 2-mercaptomethylglutaric acid, dimethyl 2-mercaptomethylglutarate, diethyl 2-mercaptomethylglutarate, diisopropyl 2-mercaptomethylglutarate, ditertiarybutyl 2-mercaptomethylglutarate, diacetoxymethyl 2-mercaptomethylglutarate and dipivaloyloxymethyl 2-mercaptomethylglutarate.
5. A compound of claim 1 wherein X is R".
6. A compound of claim 5 wherein R" is

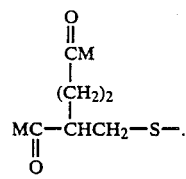

7. A Bis(2,4-dicarboxy-1-butyl) disulfide of claim 6.
8. A compound of claim 1 wherein X is

9. A compound of claim 8 wherein M is OR.
10. A compound of claim 9 selected from S-benzoyl-2-mercaptomethylglutaric acid, S-acetyl-2-mercaptomethylglutaric acid, S-propionyl-2-mercaptomethylglutaric acid, S-butyryl-2-mercaptomethylglutaric acid and S-isobutyryl-2-mercaptomethylglutaric acid.
11. A compound of claim 1 wherein M is OR and R is selected from amino cation and metal cation.
12. A compound of claim 11 wherein R is a positively charged ion selected from alkaline metal, alkaline earth metal, transition metal, gold, platinum and mixtures thereof.
13. A compound of claim 12 wherein R is selected from lithium, sodium, potassium, magnesium, calcium, strontium, chromium, manganese, iron, cobalt, nickel, copper, zinc, gold and platinum.
14. A compound of claim 13 wherein R is selected from copper, zinc, gold and platinum.
15. A compound of claim 14 wherein R is gold.
16. 2-Mercaptomethylglutaric acid.

* * * * *